United States Patent [19]
Linkous

[11] Patent Number: 5,994,268
[45] Date of Patent: Nov. 30, 1999

[54] PHOTOCATALYTIC SURFACING AGENTS WITH VARYING OXIDES FOR INHIBITING ALGAE GROWTH

[75] Inventor: Clovis A. Linkous, Merritt Island, Fla.

[73] Assignee: University of Central Florida, Orlando, Fla.

[21] Appl. No.: 09/263,309

[22] Filed: Mar. 5, 1999

Related U.S. Application Data

[62] Division of application No. 08/859,348, May 20, 1997, Pat. No. 5,880,067.

[51] Int. Cl.⁶ .......................... A01N 59/16; A01N 59/00; A01N 55/02
[52] U.S. Cl. .......................... 504/120; 504/151; 504/152; 424/646
[58] Field of Search .................... 504/120, 151, 504/152; 424/646

[56] References Cited

U.S. PATENT DOCUMENTS

| | | | |
|---|---|---|---|
| 4,654,208 | 3/1987 | Stockel | 424/78 |
| 4,788,038 | 11/1988 | Matsunaga | 422/22 |
| 4,830,657 | 5/1989 | Jakubowski | 71/67 |
| 4,863,608 | 9/1989 | Minoo | 210/638 |
| 5,098,472 | 3/1992 | Watkins | 106/15.05 |
| 5,142,058 | 8/1992 | Willingham | 548/213 |
| 5,145,587 | 9/1992 | Ishii | 210/759 |
| 5,160,527 | 11/1992 | Law | 71/67 |
| 5,192,452 | 3/1993 | Mitsui | 210/716 |
| 5,220,108 | 6/1993 | Hashimoto | 588/208 |
| 5,223,149 | 5/1996 | Antelman | 210/764 |
| 5,244,811 | 9/1993 | Matthews | 436/146 |
| 5,245,112 | 9/1993 | Hoshimoto | 588/206 |
| 5,246,737 | 9/1993 | Muradov | 427/404 |
| 5,254,526 | 10/1993 | Hamilton | 504/119 |
| 5,290,601 | 3/1994 | Brooks | 427/412.4 |
| 5,302,192 | 4/1994 | McLearie | 106/18.33 |
| 5,322,508 | 6/1994 | Foster | 210/711 |
| 5,352,444 | 10/1994 | Cox | 424/76.5 |
| 5,374,599 | 12/1994 | Ishii | 502/326 |
| 5,490,941 | 2/1996 | Miyabe | 210/673 |
| 5,501,801 | 3/1996 | Zhang | 210/48 |
| 5,518,992 | 5/1996 | Linkous | 504/151 |
| 5,541,096 | 7/1996 | Nomura | 435/176 |
| 5,547,823 | 8/1996 | Murasawa | 430/531 |
| 5,587,157 | 12/1996 | Cox | 424/76.5 |
| 5,593,737 | 1/1997 | Meinzer | 427/512 |
| 5,616,532 | 4/1997 | Heller | 502/242 |

Primary Examiner—Jose' G. Dees
Assistant Examiner—Alton Pryor
Attorney, Agent, or Firm—Brian S. Steinberger; Law Offices of Brian S. Steinberger

[57] ABSTRACT

Self cleaning mixtures that use photoactive agents with varying oxides, along with mixing the photoactive agents with carbon, noble metals and cobalt phosphide that inhibit the growth of algae are disclosed. The agents include concentrations of approximately at least 5% to approximately 50% $TiO_{n1}$, $WO_{n2}$, $X$—$WO_{n2}$, or $X$—$TiO_{n1}$, where $1.8 \leq n1 \leq 2$, and where $2.2 \leq n2 \leq 3$, and where X can be one of carbon, a noble metal, and cobalt phosphide. The agents can be combined together, and/or each agent can be combined with various coatings such as but not limited to a cement or a polymer binder. The coatings and agents can be applied to surfaces that are exposed to water such as but not limited to an aquarium, liners on the inner walls of swimming pools, drinking water tanks and the like. Further, applications can include using the novel surfacing agent as part of a solar water heater for both a home and a pool, wherein in the latter application the heater is connected between pool pumps and the pool so that when light is absorbed inside the heater, the surfacing agent becomes active for inhibiting the growth of algae. The photoactive agent can also be applied as a non-toxic algae-retardant marine paint. The invention can be used to inhibit the growth of other undesirable substances such as fungus, bacteria and mold.

6 Claims, 1 Drawing Sheet

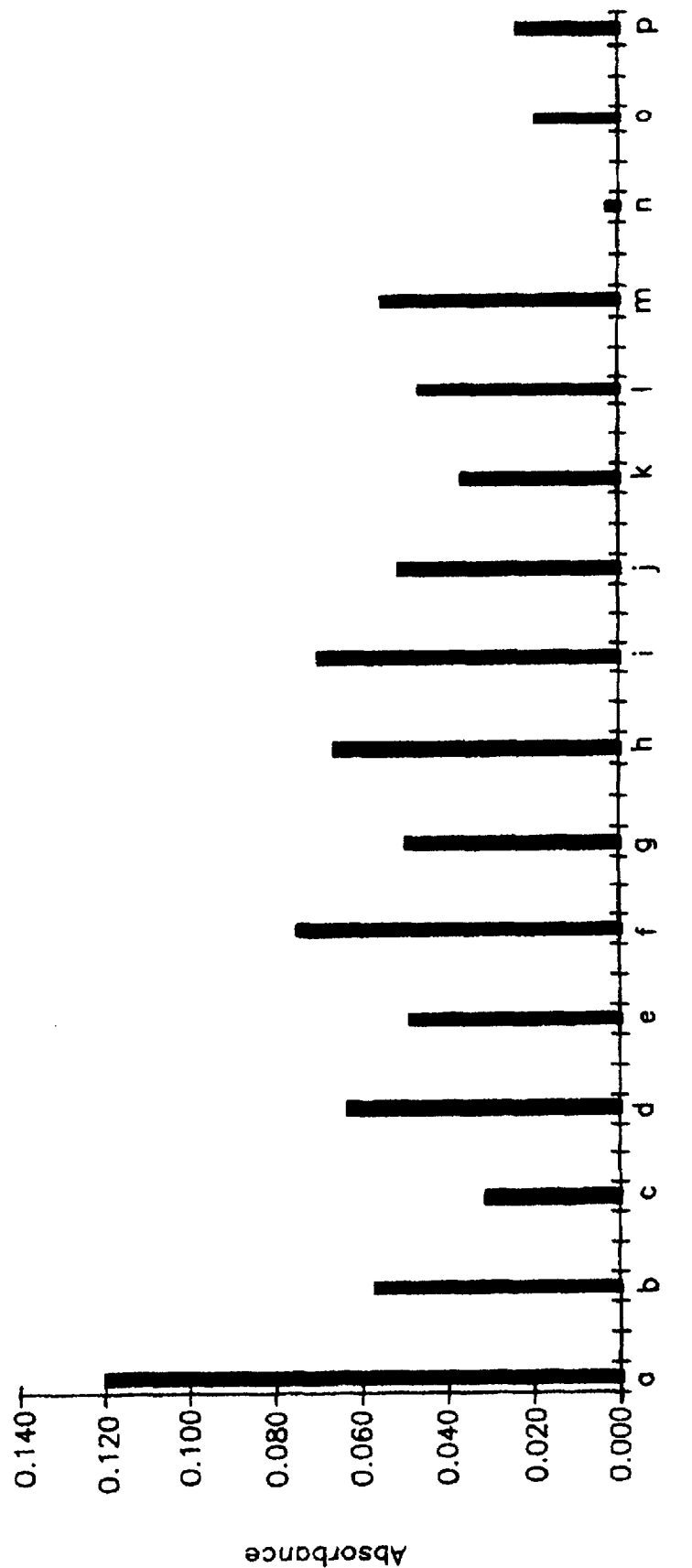

PHOTOCATALYTIC SURFACING AGENTS WITH VARYING OXIDES FOR INHIBITING ALGAE GROWTH

This is a Divisional of application Ser. No. 08/859,348 filed May 20, 1997 now U.S. Pat. No. 5,880.067.

This invention relates to inhibiting the growth of fresh water and sea water plant life, and in particular to self cleaning photocatalytic surfacing agents that vary the oxides of photocatalysts such as titanium dioxide and tungsten trioxide, combining the agents with co-catalyst agents such as Carbon, Cobalt Phosphide and noble metals, and methods of applying these agents to inhibit the growth of nuisance organisms such algae type plants, bacteria, mold and fungus. This invention relates to U.S. Pat. No. 5,518,992 issued on May 21, 1996 by the same inventor thereof, whose subject matter is incorporated by reference.

BACKGROUND AND PRIOR ART

Undesirable nuisance plant growth such as algae, bacteria, mold and fungus, have been a common problem for surfaces in both fresh water and seawater areas. For example, swimming pools, fountains and other manmade vessels that hold water are subject to fouling by algae.

Past methods for preventing algae type plants have had numerous problems. Current surfacing agents for treating algae growth are basically toxins that also can be toxic to humans above threshold concentrations. For example, tributyl tin has been shown to be an effective toxin and has been incorporated into marine based paints for the hulls of boats. While gradual release of the toxin when the boat is underway is considered acceptable, a boat in port can generate unacceptable concentrations of toxin.

Certain preparations of Titanium Dioxide can be bright white in color, and are often used in commercial paint formulations. See U.S. Pat. No. 5,142,058. However, these preparations are made deliberately so as to be photo-inactive where any form of photo-activity is regarded as a negative characteristic, because the organic binder containing the pigment can be ultimately attacked and destroyed.

A standard toxin agent includes chlorine. Chlorine is a standard means for disinfecting swimming pool water and drinking water. However, disinfectants such as chlorine become spent and must be replaced over time with repetitive additional costs. Heavy chlorination of microorganism-containing water can also result in suspected carcinogenic by-products such as trihalomethanes.

Toxin release agents are not only inferior due to their health effects on higher order plants and animals, but also because they represent a consumable item that must be eventually replaced.

Many types of algicides function as light blockers, absorbing the light necessary for algae growth. This involves dissolving one or more dyes in the water whose net absorption spectrum matches that of the algae. Thus, the water is dyed with an unnatural shade of blue or green that can be aesthetically unappealing. These algacides are also subject to eventual decomposition and require periodic replenishment.

Photocatalysts have been used for the decomposition of organics. See U.S. Pat. Nos. 4,863,608 to Kawai; 5,244,811 to Matthews; 5,332,508 to Foster; 5,501,801 to Zhang; 5,541,096 to Nomura; 5,547,823 to Murasawa; 5,593,737 to Meinzer et al.; and 5,616,532 to Heller et al. However, these patents are limited to requiring specific oxide values of $TiO_2$ and $WO_3$. None of these patents varies the oxides themselves.

SUMMARY OF THE INVENTION

The first objective of the present invention is to provide a surfacing agent for inhibitiing nuisance organisms including algae, bacteria, mold and fungus.

The second object of this invention is to provide a method for inhibiting the growth of nuisance organisms including algae, bacteria, mold and fungus, that is nontoxic to humans.

The third object of this invention is to provide a method for inhibiting the growth of nuisance organisms including algae, bacteria, mold and fungus, that is photocatalytic and becomes active with light.

The fourth object of this invention is to provide a method for inhibiting the growth of nuisance organisms including algae, bacteria, mold and fungus, that can remain active indefinitely over time whenever light is available.

The fifth object of this invention is to provide a method for inhibiting the growth of nuisance organisms including algae, bacteria, mold and fungus, that does not need constant replacement nor replenishment to remain active.

The sixth object of this invention is to provide a method of inhibiting the growth of nuisance organisms including algae, bacteria, mold and fungus, without having to artificially color the water with algacidal dyes.

The seventh object of this invention is to provide an economical one-time cost for controlling the growth of nuisance organisms including algae, bacteria, mold and fungus.

The inventor of the subject invention has shown that Titanium Dioxide $TiO_2$ and $WO_3$ have been shown to be useful as a photocatalytic surfacing agent for inhibiting algae growth. See U.S. Pat. No. 5,518,992 to Linkous which is incorporated by reference.

The invention includes self cleaning mixtures that combine photoactive agents along with surface coatings together inhibit the growth of algae when light is applied. The mixtures can include concentrations of an agent selected from approximately at least 5% to approximately 50%l or more $TiO_{n1}$, where $n1 \leq 2$, $WO_{n2}$, where $n2 \leq 3$. combinations thereof with carbon(C), noble metals(Ir, Pt), and cobalt phosphide $CO_2P$ as accelerator co-catalysts. The co-catalysts lower the kinetic reaction energy by changing the relative adsorption enthalpy of the reactants(water & oxygen). These mixtures can be combined with one another and/or further combined with various coatings such as but not limited to a cement or a polymer binder, or a plastic, fiberglass, ceramic and the like.

The coatings and agents can be applyed and/or painted to surfaces that are exposed to water such as but not limited to an aquarium, liners on the inner walls of swimming pools, roofs, painted surfaces, and the like. Further, applications can include using the novel surfacing agent as part of a solar water heater for both a home and a pool, wherein in the latter application the heater is connected between pool pumps and the pool so that when light is absorbed inside the heater, the surfacing agent becomes active for inhibiting the growth of algae. The photoactive agent can also be applied as a non-toxic algae-retardant marine paint.

The invention can inhibit the growth of nuisance organisms such as algae, mold, fungus and bacteria that grow on surfaces within water, moisture, condensation and humid type environments.

Further objects and advantages of this invention will be apparent from the following detailed description of a presently preferred embodiment which is illustrated schematically in the accompanying drawings.

BRIEF DESCRIPTION OF THE FIGURES

FIG. 1 is a graph comparison of Algae Growth on sixteen(16) Photocatalytic Substrates.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

FIG. 1 is a graph comparison of Algae Growth on sixteen(16) Photocatalytic Substrates. The sixteen photocatalytic substrates are described in reference to TABLE 1.

TABLE 1

| | |
|---|---|
| a. | $WO_3$ |
| b. | $TiO_2$ (Fisher Brand) |
| c. | Pt-$TiO_2$ |
| d. | Pt-$WO_3$ |
| e. | Ir-$TiO_2$ |
| f. | Ir-$WO_3$ |
| g. | 1% carbon blended with $TiO_2$ |
| h. | 3.8% carbon blended with $TiO_2$ |
| i. | 50% carbon blended with $TiO_2$ |
| j. | 1:1 weight ratio of $WO_3$ to $TiO_2$ |
| k. | Reduced $WO_n$ where n < 3 |
| l. | 1% carbon blended with $WO_3$ |
| m. | 4.8% carbon blended with $WO_3$ |
| n. | 50% carbon blended with $WO_3$ |
| o. | 1% $Co_2P$ (cobalt phosphide) blended with $TiO_2$ |
| p. | 4.8% $Co_2P$ (cobalt phosphide) blended with $TiO_2$ |
| q. | 50% $Co_2P$ (cobalt phosphide) blended with $TiO_2$ |

The breakdown of the different photocatalysts will now be described. Pt—$WO_3$ refers to platinized tungsten oxide. Pt—$TiO_2$ refers to platinized titanium dioxide. $TiO_2$ used was from Fisher Scientific Company, USA. $WO_3$ used was from Aldrich, USA. Pt(platinum) and Ir(iridium) was from Aldrich, USA. C (carbon) used was Vulcan XC72, a common fuel cell grade carbon, manufactured by Cabot, USA. $CO_2P$ (cobalt phosphide) used was an insoluble material, manufactured by Cerac, USA.

The experimental set-up for testing the sixteen(16) test samples will now be described. The substrate used for the experiment was applied to a one inch square marcite material(portland cement). The compositions were hand-mixed by preparing approximately 100 mg of photocatalyst per square inch of material and approximately 300 to approximately 500 mg per square inch of a binder solution. The binder used was Thompson's Water Seal manufactured by Thompson Inc., USA. The substrates with agents were deposited and vertically supported within a ten gallon freshwater aquarium stocked with live tropical fish. The light source combination used was two four foot, 40 Watt fluorescent bulbs having a broadband, white light wavelength ditribution along with two black light bulbs that gave out a narrow bandwidth centered at approximately 365 nm Analysis of the samples was done after three days. Each of the preparations represented in FIG. 1 were soaked in a measured volume of acetone. The absorbence of these solutions at 662 nm corresponds to the absorption maximum of chlorophyll. Absorbance measuring was done using a Spectro-photometer model 601 manufactured by Spectronics Inc., USA. Approximately 100 milligrams of agent(as represented by samples (a) through (p) in FIG. 1) was applied per square inch of substrate, with surface coatings being less than approximately 1 mm. Each of the bars represented in FIG. 1 was an average taken of three tests each. Testing was conducted in May, 1997 at the Florida Solar Energy Center, Cocoa, Fla.

FIG. 1 shows that the growth of algae has inhibited in all applications. In FIG. 1, the vertical axis has absorbance at 680 nm. Referring to FIG. 1, samples (b) $TiO_2$ (0.059); (c) Pt—$TiO_2$ (0.030); and (d) Pt—$WO_3$ (0.061) show greater algae growth inhibition than sample (a)$WO_3$ (0.12).

From FIG. 1, the lower the absorbance value the greater the inhibiting of algae growth.

Referring to FIG. 1, samples (e) Ir—$TiO_2$; and (f) Ir—$WO_3$ show that using co-catalyst Ir(iridium) further accelerates inhibiting algae growth. Both Pt and Ir are noble metals. Clearly, other noble metals including palladium(Pd), gold(Au), ruthenium(Ru) and osmium(Os), can be used in combination with the photocatalysts $TiO_2$ and $WO_3$ to accelerate inhibiting algae growth.

Samples (g), (h), (i), (l), (m) and (n) are evidence that using carbon(C) in combination with the photocatalysts $TiO_2$ and $WO_3$, further inhibit the growth of algae type organisms. Furthermore, the best results come from using approximately a 1% carbon(C) with these photocatalysts, where the total weight percent is 1% C and 99% photocatalyst($TiO_2$ &/or $WO_3$).

Sample (j) represents that the 1:1 combination of photocatalysts $TiO_2$ and $WO_3$ further inhibit the growth of algae type organisms.

Sample (k) represents reduced $WO_3$. Using $WO_n$ where $2.2 \leq n \leq 3$ in sample (k) shows an absorbance value of less than approximately 0.040, while sample (a) representing $WO_3$ shows an extremely high absorbance value of approximately 0.120. Again the lower the absorbance value the greater the inhibiting effect of algae growth. Reducing the oxide from 3 to a lower value can be done several ways. Reduced oxide $WO_3$ which is approximately $WO_{2.9}$ can be purchased from Avocet Co. of California, USA, and U.S. Tungsten Corp., USA.

Furthermore, $WO_3$ can have their oxide value reduced to $WO_n$, where $2.2 \leq n < 3$, bay being heated in an hydrogen atmosphere to approximately 400C. until the normal greenish color of $WO_3$ changes to a dark blue. Known treatises state that tungsten blue oxide tint occurs within this range. See Advanced Inorganic Chemistry, by Cotton & Wilkinkson, Wiley & Sons, 3rd. Edition, 1972, pages 947; and Constitution of Binary Alloys, by Shunk; McGraw Hill, 2nd Supp. 1969, page 586.

The algae inhibiting effects of oxygen removal can be analogized to have similar results for $TiO_{n2}$, where $1.8 \leq n2 < 2$. As compared to the effects of $TiO_2$, reducing the oxygen(oxide) content by approximately 10% here should enhance inhibiting the growth of algae. The effects of varying the oxide number down will now be explained. The creation of lattice vacancies at the particle surface provides catalytic adsorption sites for water splitting. Thus, the lower the oxygen number(i.e. $TiO_{n2}$, where $1.8 \leq n2 < 2$ as compared to $TiO_2$), the greater the density of catalytic sites at the particle surface. Going below this number causes the lattice to become too unstable, where the lattice structure can revert to nonphotocatalytic phases. See Constitution of Binary Alloys, by Shunk, McGraw Hill, 2nd Supp. 1969, pages 577–578.

Referring to FIG. 1, samples (o) 1% $Co_2P$ (cobalt phosphide) blended with $TiO_2$; (p) 4.8% $CO_2P$ (cobalt phosphide) blended with $TiO_2$; and (q) 50% $Co_2P$ (cobalt phosphide) blended with $TiO_2$ represent that cobalt phosphide is a good co-catalyst that can be used with photocatalyst such as $TiO_2$ and $TiO_3$. Similar to the results of samples (g) and (1), here only approximately 1% $Co_2P$ achieved the best results of inhibiting the growth of algae.

Clearly, since algae is a stubborn type nuisance organism, the applications shown in FIG. 1, would also apply to other nuisance organisms such as but not limited to bacteria, mold, and fungus, that grow in fresh water, salt water, brackish water, and also occur under moisture, humidity and condensation conditions.

While the agents in FIG. 1 were applied to cement type material, the invention can applied to other surface substrates such as but not limited to marcite, glass, ceramic, fiberglass, plastic, wood, combinations, thereof, and the like.

Under conditions conducive to algae growth, clean surfaces coated with photocatalytic agents will resist the spread of algae onto themselves.

From the testing that has occurred as represented in FIG. 1, algae inhibition can occur as low as 5% by weight for photocatalysts $TiO_2$ and $WO_3$. Surface coatings of <1 mm thickness may need 40 to 50% or more $TiO_2$ and $WO_3$, of which approximately 1% can include other co-catalyst accelerator agents such as carbon, noble metals and cobalt phosphide. Other surface coatings and mixtures that can be included with $TiO_2$ and $WO_3$, include polymers such as polymethyl methacrylate, polycarbonate and white portland cement. $TiO_2$ and $WO_3$ can be blended together with types of cement and water according to cement vendor's instructions. $TiO_2$ and $WO_3$ can be blended together with types of polymers by applying a pure polymer coating then softening with solvents such as dichloroethane and feathering the photoactive powder into the surface.

The various photoactive surfacing agents disclosed above can be mixed together and used without reducing the performance of the individual components. Furthermore a potential synergistic effect can be realized when combining together agents such as but not limited to $TiO_2$ and $WO_3$ together in one mixture.

The surfacing agents can be used in applications such as but not limited to non-toxic algae-retardant marine paint, surfacing agents on light-stricken walls in an aquarium, surfacing agent for lining the inner walls of swimming pools, roofs, painted surfaces and the like. Further, applications can include using the novel surfacing agent as part of a solar water heater for either or both a home and a pool. In a pool application, the surfacing agent is applied to an inner wall within the heater that is connected between pool pumps and the pool so that when light is absorbed inside the heater, the surfacing agent becomes active for inhibiting the growth of algae.

Although the invention has been described as being used to inhibit the growth of algae, the invention can be used as a bacterial control for disinfection of water for drinking or bathing.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of inhibiting the growth of nuisance organisms including algae, bacteria, fungus and mold, on surfaces that are exposed to water using a photoactive coating comprising the steps of:

(a) applying a coating combined with a photoactive agent having a $Co_2P$ compound to a water exposed surface;

(b) applying light to the coating and the agent which inhibits the growth of nuisance organisms on the surface.

2. The method of inhibiting the growth of nuisance organisms of claim 1, wherein the photoactive agent includes:

$TiO_n$, wherein $n \leq 2$.

3. The method of inhibiting the growth of nuisance organisms of claim 2, wherein n includes:

$1.8 \leq n \leq 2$.

4. The method of inhibiting the growth of nuisance organisms of claim 1, wherein the photoactive agent includes:

$WO_n$ to a water exposed surface, wherein $n \leq 3$.

5. The method of inhibiting the growth of nuisance organisms of claim 4, wherein n includes:

$2.5 \leq n \leq 3$.

6. The method of inhibiting the growth of nuisance organisms of claim 5, wherein the $Co_2P$ includes:

approximately 1% $Co_2P$.

* * * * *